United States Patent [19]

Sakamoto

[11] Patent Number: 4,465,375
[45] Date of Patent: Aug. 14, 1984

[54] METHOD AND DEVICE FOR MEASURING A HALFTONE DOT AREA RATE OR A HALFTONE PICTURE DENSITY

[75] Inventor: Takashi Sakamoto, Kyoto, Japan
[73] Assignee: Dainippon Screen Seizo Kabushiki Kaisha, Kyoto, Japan
[21] Appl. No.: 259,080
[22] Filed: Apr. 30, 1981
[30] Foreign Application Priority Data May 1, 1980 [JP] Japan ................................ 55-57082

[51] Int. Cl.³ ..................... G01N 21/01; G01N 21/55
[52] U.S. Cl. ..................................... 356/434; 356/445
[58] Field of Search ...................... 356/430, 432–434, 356/443–445

[56] References Cited

U.S. PATENT DOCUMENTS 3,053,181  9/1962  Jorgensen ............................ 356/445
3,375,751  4/1968  Engborg et al. ...................... 356/443
3,393,602  7/1968  Stouffer ................................ 356/445
4,264,210  4/1981  Mitsuhashi .......................... 356/432
4,371,265  2/1983  Mitsuhashi .......................... 356/432

*Primary Examiner*—Bruce Y. Arnold
*Attorney, Agent, or Firm*—Michael A. Painter

[57] ABSTRACT

A method for measuring a halftone dot area rate or a halftone picture density in a densitometer or half-tone dot area rate measuring means. A light beam is emitted by a light source and impinges upon an object to be measured. The light beam passes through or is reflected from the object to be measured and is received by a photoelectric element. A weighting of the light beam is performed by a weighting means so that the assigned weigth is substantially large at its central part and is reduced radially to its periphery, the reduction depending upon a transmittance or a reflectance of the object.

3 Claims, 18 Drawing Figures

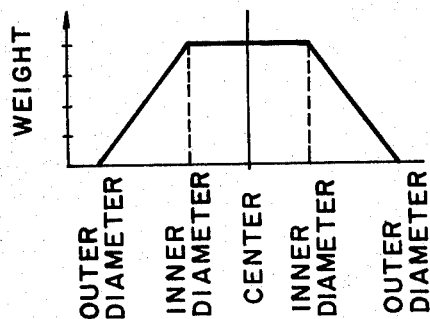
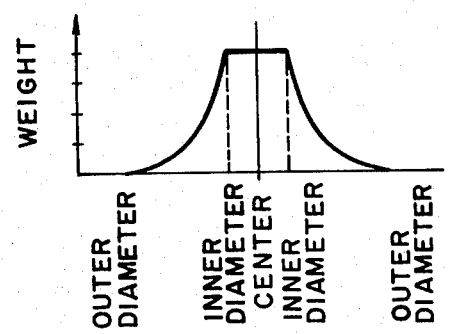
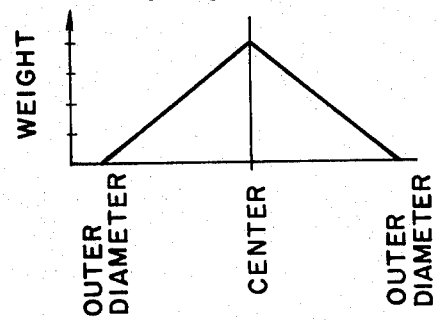
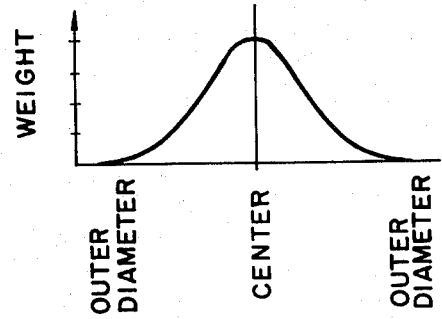
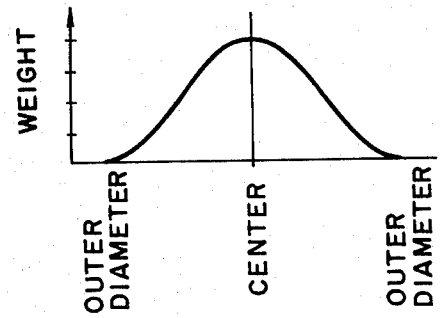
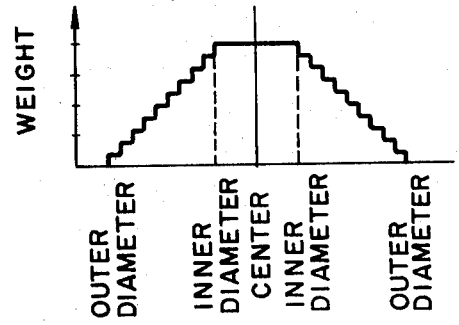
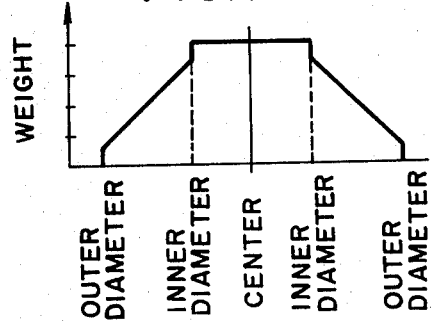

METHOD AND DEVICE FOR MEASURING A HALFTONE DOT AREA RATE OR A HALFTONE PICTURE DENSITY

BACKGROUND OF THE INVENTION

The present invention relates to a method for measuring a halftone dot area rate or a halftone picture density.

In a conventional halftone dot area rate measuring means, since the gradation of a measured halftone picture image varies, the aperture diameter which will determine the measured area is preferably small. However, if it is too small, when the halftone picture image is measured, the value which is measured will vary depending on the relative position of the aperture and the halftone dot.

Large variances do not arise when the number of scanning lines per distance increment is large. Large variances often occur when the number of scanning lines is small, e.g., a gauge having about ten lines per centimeter for printed matter. Such a gauge is printed in a relatively small area such as 5 mm×6 mm, and hence this problem can be resolved only by expanding the diameter of the aperture or the measuring area.

SUMMARY OF THE INVENTION

It is an object of the present invention to provide a method for measuring a halftone dot area rate or halftone picture density in a densitometer or halftone dot area rate measuring means free from the aforementioned inconveniences, which is stable and reliable, and which is capable of measuring an area which is small when compared with a screen pitch.

It is another object of the present invention to provide a device for measuring a halftone dot area rate or halftone picture density in a densitometer or halftone dot area rate measuring means free from the aforementioned inconveniences, which is stable and reliable, and which is capable of measuring an area which is small compared with a screen pitch.

According to the present invention there is provided a method for measuring a halftone dot area rate or halftone picture density in a densitometer or halftone dot area rate measuring means. Pursuant to the present invention, a light beam generated by a light source is incident to an object to be measured. The light beam is passed through or is reflected from the object and is received by a photoelectric element. In operation, the light beam passing through or reflected from the object is weighted so that the weight is large in its central part and is reduced radially to its periphery depending on the transmittance or the reflectance of the object.

The present invention constitutes a device for measuring a halftone dot area rate or halftone picture density in a densitometer or halftone dot area rate measuring means. A light beam generated by a light source is incident to the object to be measured. The light beam passes through or is reflected from the object and is received by a photoelectric element. The light beam passing through or reflected from the object is weighted so that the weight is large in its central part and is reduced radially to its periphery depending on a transmittance or reflectance of the object.

BRIEF DESCRIPTION OF THE DRAWINGS

Other objects and features of the present invention will be clear from the following description of preferred embodiments of the present invention with reference to the accompanying drawings, in which:

FIG. 1 showing a conventional type, and FIG. 2 showing a type according to the present invention;

FIG. 3 showing a conventional type, and FIG. 4 and FIG. 5 showing essential alternative embodiments in accordance with the present invention;

FIG. 7—the center of the aperture is coincident with the center of a light part of the halftone dots;

FIGS. 9–15 show various weight characteristic curves for correcting errors in measured density values;

DESCRIPTION OF THE PREFERRED EMBODIMENTS

Figure 1:
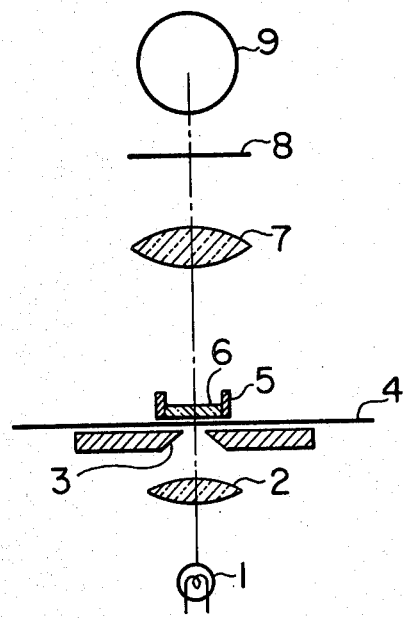
FIGS. 1 and 2 are schematic views of optical systems for a transmission densitometer or a halftone dot area rate measuring means.
Figure 2:
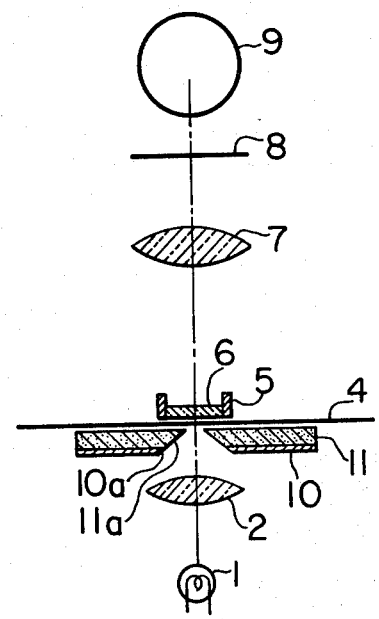

FIGS. 1 and 2 illustrate optical systems employing conventional transmission densitometer or halftone dot area rate measuring means, and a transmission densitometer or halftone dot area rate measuring means according to the present invention, respectively.

The apparatus in FIG. 1 comprises a light source 1 such as an incandescent lamp, a first condenser lens 2, an aperture plate 3 made of a light-shielding material having an aperture therethrough, a diffusion plate 6 surrounded by a guide 5 which prevents the ambient light from coming in, a second condenser lens 7, a filter for correcting spectral characteristics, and a photoelectric element 9 such as a photomultiplier. All are aligned along a light axis. The object 4 to be measured is disposed between guide 5 and aperture plate 3. The aperture edge of the aperture plate 3 is tapered away from the light source 1 and it is adapted to be formed so that a luminous energy distribution over a measured surface may be uniform regardless of the thickness of the aperture plate 3.

In this embodiment, the light beam generated by the light source 1 is converged by the first condenser lens 2 and then passes through the aperture of the aperture plate 3. The measuring area is determined by the aperture. The light beam emitted through the aperture then passes through the object 4. The luminous energy of the light beam is decreased depending on the transmittance of the object 4 when it passes through the object. After passing through object 4, the attenuated light beam is directed to the receiving section. In the light receiving section, the ambient light is prevented from coming therein by the guide 5 and thus only the light beam through the aperture is incident. The light beam is diffused in the diffusion plate 6 and a surrounding light shield tube (not shown). Then, the diffused light beam is converged by the second condenser lens 7 and its spectral characteristics are corrected by the filter 8. Finally, the corrected light beam is incident to the photoelectric element 9.

The photoelectric current which is proportional to the transmittance of the object 4, is obtained in the photoelectric element 9. When the photoelectric current is fixed, the photoelectric voltage obtained in the photoelectric element 9 is proportional to the transmission density of the object 4. Thus the photoelectric current or voltage which is obtained is then converted into a halftone dot area or a halftone picture density.

Figure 3:
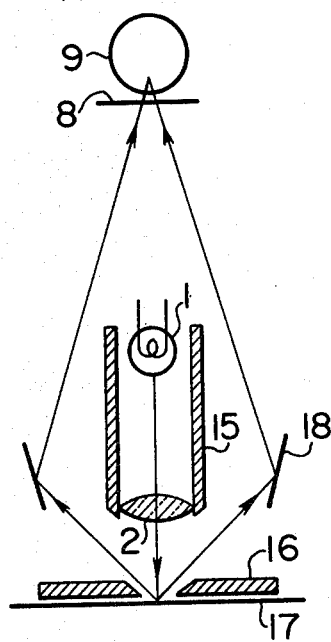
FIGS. 3–5 are schematic views of optical systems for a reflection densitometer or a halftone dot area rate measuring means.
Figure 4:
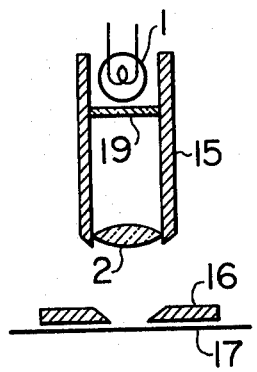
Figure 5:
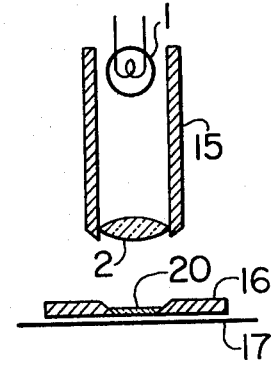

An optical system employing a conventional reflection densitometer or halftone dot area rate measuring means is shown in FIG. 3, and a system employing reflection densitometers or halftone dot area rate measuring means according to the present invention are shown in FIGS. 4 and 5.

Referring to FIG. 3, object 17 is aligned with: an aperture plate 16 having an aperture therethrough, having same shape and functions as that shown in FIG. 1; the condenser lens 2 and the light source 1; a light shield tube 15 for shielding the light generated by the light source 1; a frustum tubular mirror 18; the correction filter 8; and the photoelectric element 9. All are aligned along the light axis so that the frustum tubular mirror 18 may reflect to the photoelectric element 9 via the filter 8 the light beam which is incident from the light source 1 to the object 17, and is then reflected by the object 17.

In this embodiment, when the light beam is reflected by the object 17, the luminous energy of the light beam declines depending on the reflectance of the object.

As described above, the photoelectric current obtained in the photoelectric element 9 is proportional to the reflectance of the object 17. When the photoelectric current is fixed, the photoelectric voltage obtained in the photoelectric element 9 is proportional to the reflection density of the object 17. Thus the obtained photoelectric current or voltage is then converted into the halftone dot area rate or the halftone picture density, in the same manner as described above.

Figure 6:
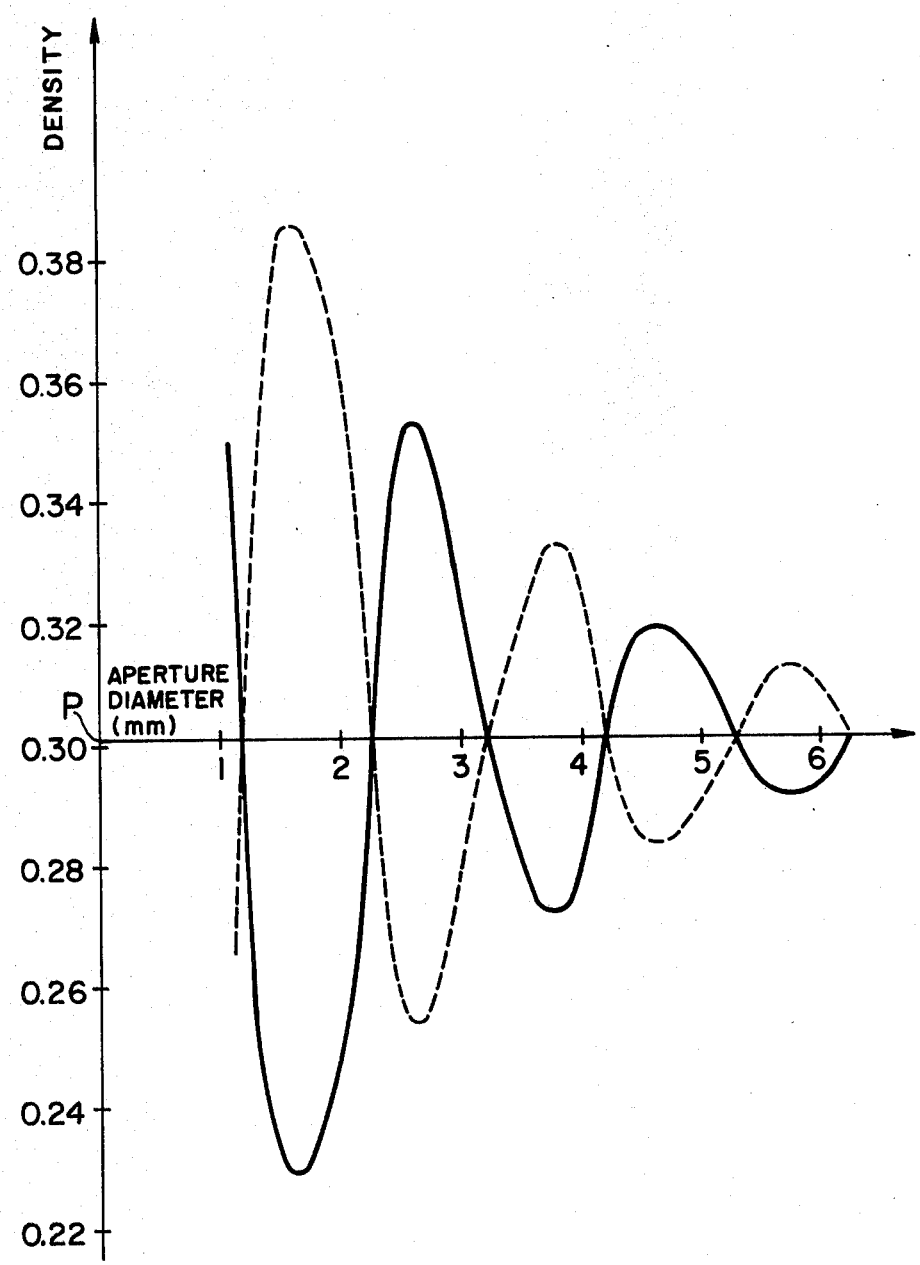
FIG. 6 shows density value curves of a halftone dot having a screen pitch of one millimeter and a halftone dot area rate of 50%, plotted with respect to aperture diameter; solid and broken lines indicate the positional relationship between the aperture and the halftone dots, as shown in FIGS. 7 and 8, respectively.
Figure 7:
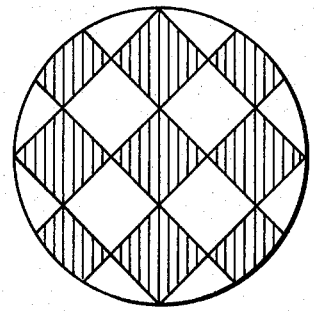
FIGS. 7 and 8 show the positional relationship between the aperture and the halftone dots.
Figure 8:
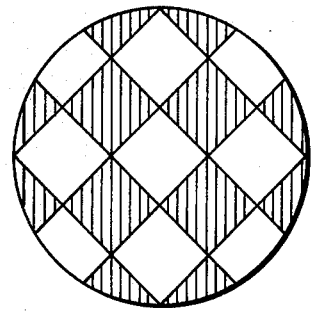
Figure 16:
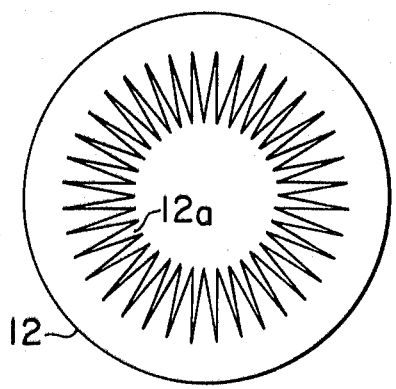
FIG. 16 shows one embodiment of an aperture having the weight characteristics shown in FIG. 9.
Figure 17:
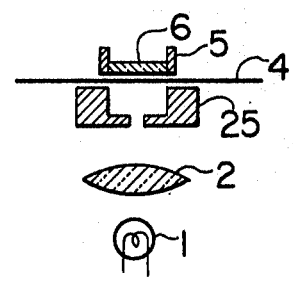
FIGS. 17 and 18 show two arrangements of the apertures in light projecting and receiving sides of the optical system, by which the weight decreases from the center to the periphery.
Figure 18:
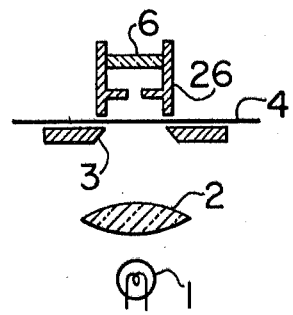

FIG. 6 illustrates the density value curves of halftone dots having a screen pitch of one millimeter and a halftone dot area rate of 50%. The curves are obtained by varying the diameter of the aperture 3 or 16. The curve represented by a solid line is obtained when the center of the aperture is coincident with the center of a light part of the halftone dot, as shown in FIGS. 7 and 8, respectively.

From FIG. 6, it is readily understood that the measured error of the halftone dot density becomes zero periodically. A point A for the aperture diameter, at which the measured error is zero, can be expressed as a function of the screen pitch P by the following formula (1), wherein n is a positive integral number:

$$A = P \times (n + 0.25) \tag{1}$$

The values for the aperture diameter A and screen pitch P are measured in millimeters. This means that when the halftone dots having the halftone dot area rate of 50% are reproduced, a group of aperture diameter values exist of which the ratio of the dark and the light parts of the halftone dot pattern is unity.

Further, when the aperture 3 or 16 employs one of such diameter values, it is ascertained that, even when the center of the aperture is not coincident with the dark or the light part of the halftone dot, the dispersion of the measured values is very small.

According to the present invention, since the measured error of the halftone dot density values varies periodically to the positive and the negative sides, as shown in FIG. 3, in order to improve the accuracy of the measurement, a weighting of the light beam passing through or reflected from the object to be measured is performed so that the weight will be substantially large in its central part and is reduced radially to its periphery depending on the density, transmittance or the reflectance of the object.

A plurality of weight characteristic curves are shown in FIGS. 9-15. The diameter of the light beam is taken in the horizontal axis, and the diameter of the central circle part is assigned the largest weight. The diameter of the light beam is hereinafter referred to as "an inner diameter" of "an inner circle" and "an outer diameter."

In the weight characteristics curve of FIG. 9, the assigned weight is largest in the inner diameter of the inner circle and linerally decreases to the outer diameter which has a value of zero.

In the weight characteristics curve of FIG. 10, the assigned weight is largest in the inner diameter of the inner circle and decreases nonlinearly (linearly with respect to its density value) to the outer diameter which has a value of zero.

In the weight characteristics curve of FIG. 11, the assigned weight is largest in the center and is linerally reduced to the outer diameter which has a value of zero.

In the weight characteristics curve of FIG. 12, the assigned weight is largest in the center and decreases exponentially (the Gaussian distribution or normal distribution) to the outer diameter which has a value of zero.

In the weight characteristics curve of FIG. 13, the assigned weight is largest in the center and is reduced along a sine wave form to the outer diameter which has a value of zero.

In the weight characteristics curve of FIG. 14, the assigned weight is largest in the inner diameter of the inner circle and decreases in a step pattern to the outer diameter which has a small value.

In the weight characteristics curve of FIG. 15, the assigned weight is largest in the inner diameter of the inner circle and is decreased by a small amount at the outer periphery of the inner circle, and then is linerally reduced to the outer diameter which has a small value.

The weight characteristics curves are, of course, not restricted to these examples. Many other examples including combinations of the entire and the partial features of the examples described above and partial modifications thereof, can be practiced according to the present invention.

In a densitometer or halftone dot area rate measuring device having an optical system of a scanning type, the weighting described above may be performed by changing the optical system, or by digitizing a photoelectric signal obtained and then performing the weighting of the digital signal according to a weight characteristics curve such as one shown in FIGS. 9-15 by using a microcomputer, or the like, without changing the optical system, thereby obtaining the density or the area rate of the halftone dot. However, these methods may require high costs.

According to the present invention the weighting is carried out, in principle, by using an optical system for a usual densitometer or halftone dot area rate measuring

TABLE

| Screen Pitch | 1 mm (10 lines/cm) | | 0.391 mm (25.6 lines/cm) | |
| --- | --- | --- | --- | --- |
| | Max. | Min. | Max. | Min. |
| Conventional Method Outer diameter 4.5 mm | 0.318 | 0.285 | 0.304 | 0.298 |
| Present Method Inner diameter 4.0 mm Outer diameter 4.5 mm | 0.302 | 0.300 | 0.303 | 0.299 |

(The density of a halftone dot having a halftone dot area rate of 50% is 0.301).

It is readily understood from this table that the measured errors according to the present invention are smaller than those which would result according to the conventional methods.

Although the present invention has been described with reference to preferred embodiments in connection with the accompanying drawings, however, various changes and modifications can be made by those skilled in the art without departing from the scope of the present invention.

What is claimed is:

1. A method for measuring a halftone dot area rate or halftone picture density in a densitometer or halftone dot area rate measuring means comprising the steps of:
   (a) emitting a light beam generated by a light source to an object to be measured;
   (b) receiving the light beam passing through or reflected from the object by a photoelectric element; and
   (c) weighting the intensity of the light beam passing through or reflected from the object and assigning the maximum value to correspond to the center of said object, the value of said assigned weight being reduced to zero at the outer periphery of said object, the weight assigned being proportional to the transmittance or reflectance of the object.

2. A method as defined in claim 1, wherein the weighting is performed by using an aperture plate having an aperture.

3. A method as defined in claim 1 wherein the weighting is performed by varying the transmittance pattern of a film plate.

* * * * *